United States Patent [19]

Hunter

[11] 4,353,258
[45] Oct. 12, 1982

[54] COMPOUND ANGLE WEDGES FOR COUPLING ULTRASOUND INTO A CURVED SURFACE OBJECT

[75] Inventor: David O. Hunter, Richland, Wash.

[73] Assignee: Westinghouse Electric Corp., Pittsburgh, Pa.

[21] Appl. No.: 189,499

[22] Filed: Sep. 22, 1980

[51] Int. Cl.³ ............................................. G01V 29/04
[52] U.S. Cl. ................................................... 73/644
[58] Field of Search ......................................... 73/644

[56] References Cited

U.S. PATENT DOCUMENTS

| | | | |
|---|---|---|---|
| 2,984,756 | 5/1961 | Bradfield | 73/644 |
| 4,195,530 | 4/1980 | Ross et al. | 73/644 |
| 4,279,167 | 7/1981 | Erb et al. | 73/644 |

Primary Examiner—Anthony V. Ciarlante
Attorney, Agent, or Firm—F. J. Baehr, Jr.

[57] ABSTRACT

A compound angle wedge for coupling ultrasound into a turbine disc to interrogate the keyway area of the turbine disc, the compound angle wedge having a cylindrical surface which is disposed to contact the object to be interrogated and which has a double offset with respect to an interrogating transducer mounting surface.

10 Claims, 7 Drawing Figures

COMPOUND ANGLE WEDGES FOR COUPLING ULTRASOUND INTO A CURVED SURFACE OBJECT

BACKGROUND OF THE INVENTION

This invention relates to wedges for coupling ultrasound into an object, and more particularly to compound angle wedges for coupling ultrasound into a curved surface object.

Ultrasonic nondestructive inspection of metallic and other solid structures are often made utilizing Plexiglas or other solid materials as couplant wedges. The wedges are used because it is desirable to generate an ultrasonic beam propagated at an angle to the surface of the material such as an angled beam shear wave. The angles can be varied to direct the beams in certain predetermined directions, which is advantageous when searching for particular flaws in specific areas in a solid structure. Curved surfaces present special problems with respect to the shape of the wedge.

SUMMARY OF THE INVENTION

In general, a wedge for a transducer utilized to ultrasonically interrogate an internal area within a mass disposed beneath a bell-shaped outer surface, when made in accordance with this invention, comprises a central axis, a first plane passing through the central axis, a cylindrical surface generally fitted to a portion of the bell-shaped surface, and a second plane passing through the central axis and intersecting the cylindrical surface so as to form a circular line at the intersection thereof. The first and second planes are disposed to form an acute angle therebetween. The wedge also comprises a generally planar surface upon which the transducer mounts. The transducer mounting surface is contiguous with the cylindrical surface and has a centrally located point disposed thereon; a line passing through the centrally located point on the mounting surface and a point formed at the intersection of the central axis and the cylindrical surface. The line forms an acute angle with the axis. The wedge also has tapped holes for mounting the transducer so disposed that the central ray produced by the transducer is generally coincident with the line passing through the intersection of the central axis and the cylindrical surface.

BRIEF DESCRIPTION OF THE DRAWINGS

The objects and advantages of this invention will become more apparent from reading the following detailed description in conjunction with the accompanying drawings, in which.

DESCRIPTION OF THE PREFERRED EMBODIMENTS

Figure 1:
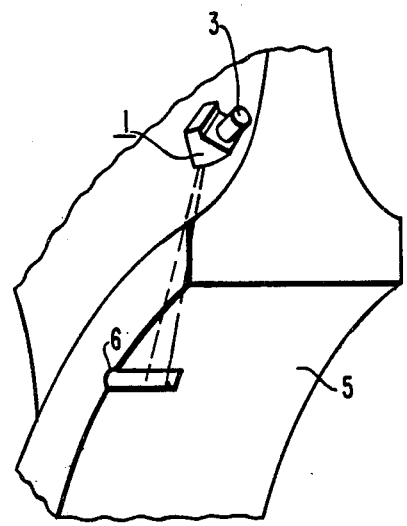
FIG. 1 is a partial perspective view showing a wedge utilized with a transducer to interrogate a keyway disposed in a turbine disc.

Referring now to the drawings in detail, and in particular to FIG. 1, there is shown a wedge 1 for a transducer 3 utilized to couple ultrasound to a mass disposed beneath a bell-shaped outer surface such as a disc 5 of a steam turbine to ultrasonically interrogate a specific area beneath the surface such as a keyway 6 from which cracks have been known to radiate.

Figure 3:
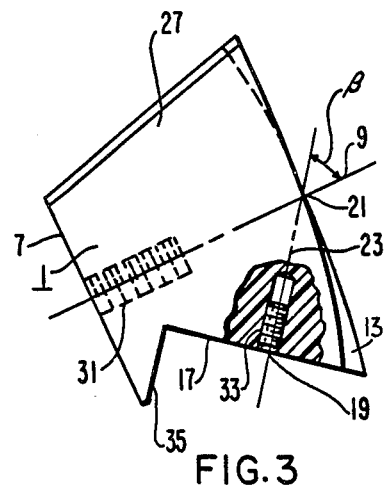
FIGS. 3 and 4 are side elevational views of the wedge shown in FIG. 2.
Figure 2:
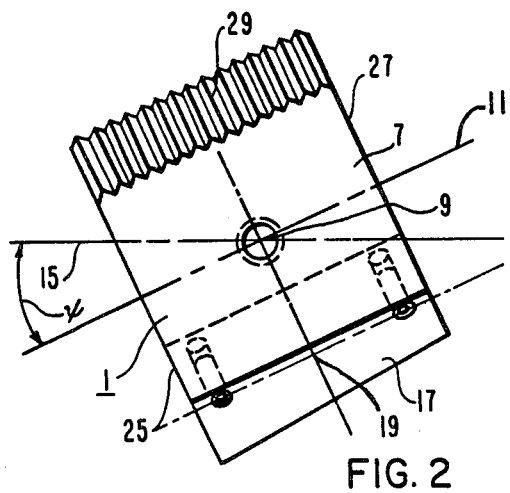
FIG. 2 is a plan view of a wedge made in accordance with this invention.
Figure 4:
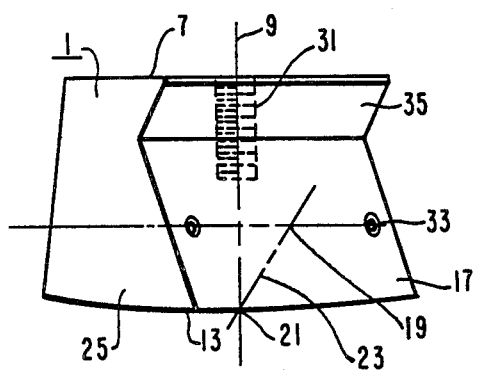

The wedge 1, as shown best in FIGS. 2 through 4, has a top surface 7, a central axis 9, disposed perpendicular to the top surface 7, and a first plane 11 passing through the central axis 9. The wedge 1 also has a cylindrical surface 13 disposed opposite the top surface 7, the cylindrical surface being generally convex and generally fits on a portion of the bell-shaped surface. However, the cylindrical surface is not identical to the bell-shaped surface. A second plane 15 also passes through the central axis 9 and intersects the cylindrical surface 13 so as to form a circular line at the intersection thereof. The first and second planes 11 and 15 are disposed to form an acute angle $\psi$ therebetween. A generally planar surface 17, upon which the transducer 3 mounts, is disposed contiguous with the cylindrical surface 13 and is so disposed to form a compound angle with respect to the second plane 15. The transducer 3 is mounted on the planar surface 17 in such a manner that the central ray produced by the transducer 3 intersects a point 19 centrally located on the planar surface 17. The intersection of the axis 9 and the cylindrical surface 13 also forms a point 21. The central ray of the transducer is generally coincident with line 23 which passes through the points 19 and 21 forming an acute angle beta ($\beta$) with the axis 9.

The wedge 1 also has a pair of generally parallel side surfaces 25 and 27 which are generally disposed perpendicular to the top surface 7. A corrugated side surface 29 having pointed corrugations is disposed opposite the transducer mounting surface 17. A tapped hole 31 is disposed in the top surface and has an axis which is coincident with the central axis 9. The transducer mounting surface 17 has a pair of tapped holes 33 disposed adjacent the side surfaces 25 and 27. The axis of the holes 33 are generally parallel to the line 23. The wedge also has another planar surface 35 contiguous with the top surface 7 and the transducer mounting surface 17 and disposed to form an acute angle with the top surface 7.

Figure 6:
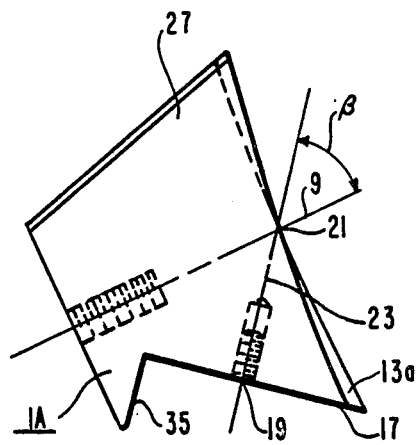
FIGS. 6 and 7 are side elevational views of the wedge shown in FIG. 5.
Figure 5:
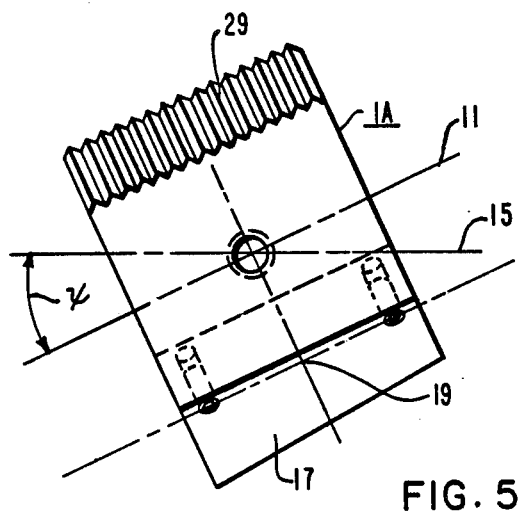
FIG. 5 is a plan view of an alternate wedge.
Figure 7:
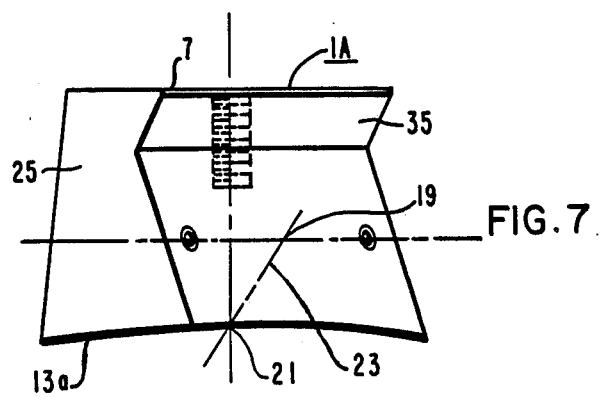

A wedge 1a shown in FIGS. 5, 6 and 7 is similar to the wedge shown in FIGS. 2, 3 and 4, the only difference being that the curved surface 13a is concave rather than convex.

In order to interrogate an area beneath the bell-shaped surface, a set of wedges is required. The set has wedges with a series of $\psi$ and $\beta$ angles and various radii for the cylindrical surface. However, the length of the line between the points 19 and 21 is fixed in order to simplify the calculations relating to the different wedges. To facilitate design of wedges for use on the many geometrically differing turbine discs, a mathematical model has been developed making it possible to quickly calculate angles $\psi$ and $\beta$. The wedges are then machined to include the $\psi$ and $\beta$ angles and then the wedges can be placed on the turbine disc so that the transducer irradiates the keyway or bore surface at a preselected angle of incidence.

The wedges hereinbefore described are easier to manufacture than wedges which exactly match the surface. Such wedges would generally be formed by lapping the wedges against the bell-shaped surface. While the wedges described hereinbefore do not exactly match the curved surface of the turbine disc, they are designed to direct the ultrasonic beam from the attached transducer at a compound angle relative to the principal axis of the disc. A compound angle is necessary because the access surface of the disc is inclined with respect to the axis of the disc and the sound beam must be directed so that it is incident at a near-tangent angle to the bore surface in order to find cracks, which radiate from the bore surface or from keyways utilized to join the disc and shaft without removing the disc from the shaft.

Compound angle wedges could be constructed by stacking two single angle wedges on top of one another. One of the wedges, the bottom single angle wedge, would have a curved surface; however, the performance of the stacked wedges will be inferior to a single structure wedge and the preferred embodiment is forming the wedge from a single mass of material.

What is claimed is:

1. A wedge for a transducer utilized to ultrasonically interrogate an internal area within a mass disposed beneath a bell-shaped outer surface, said wedge having:

a cylindrical surface generally fitting a portion of said bell-shaped surface;

a generally planar surface upon which said transducer mounts;

said cylindrical surface and said planar surface generally forming two intersecting sides of said wedge;

a central axis of said wedge being disposed along a radial line extending to said cylindrical surface and intersecting said cylindrical surface at a central point disposed on said cylindrical surface;

a plane including said central axis being disposed to intersect said cylindrical surface so as to form a circular line at the intersection thereof;

said planar surface and said plane being disposed at a compound angle with respect to each other;

said planar surface having a centrally disposed point thereon and a line being disposed between said central point on said planar surface and said point where the central axis intersects the cylindrical surface; and transducer mounting means so disposed on said planar surface that the central ray produced by said transducer is generally coincident with said line.

2. A wedge as set forth in claim 1 and also having a corrugated surface disposed contiguous with said cylindrical surface and opposite said transducer mounting surface.

3. A wedge as set forth in claim 2 wherein the corrugations in the corrugated surface are pointed.

4. A wedge as set forth in claim 1 and also having a pair of generally parallel side surfaces, said planar surface being generally perpendicular to said parallel side surfaces and said plane being disposed at an angle with respect to said parallel side surfaces.

5. A wedge as set forth in claim 1 and also having a top surface generally opposite said cylindrical surface, said axis being generally perpendicular to said top surface.

6. A wedge as set forth in claim 5 and also having a surface contiguous with said transducer mounting surface and with said top surface and forming an acute angle with said top surface.

7. A set of wedges as set forth in claim 1, the wedges having a series of angles between the plane and the parallel side surfaces and a series of angles between the line and the central axis, and the line in each wedge in the series having a fixed length between the point where it intersects the cylindrical surface and where it intersects the planar surface.

8. A series of wedges as set forth in claim 7 wherein some of the wedges have concave cylindrical surfaces and some of the wedges have convex cylindrical surfaces.

9. A set of wedges as set forth in claim 7 having cylindrical surfaces with a series of radii.

10. A set of wedges as set forth in claim 8 having cylindrical surfaces with a series of radii.

* * * * *